US 6,592,584 B2

(12) United States Patent
Agee et al.

(10) Patent No.: US 6,592,584 B2
(45) Date of Patent: Jul. 15, 2003

(54) MEDICAL DEVICE FOR CORRECTING FINGER JOINT CONTRACTURES

(75) Inventors: John M. Agee, 3700 Toronto Rd., Cameron Park, CA (US) 95682; Jeffrey Woodhouse, Sacramento, CA (US)

(73) Assignee: John M. Agee, Sacramento, CA (US); Trustee of the John M. Agee Trust dated August 15, 1996.

( * ) Notice: Subject to any disclaimer, the term of this patent is extended or adjusted under 35 U.S.C. 154(b) by 3 days.

(21) Appl. No.: 09/854,069

(22) Filed: May 9, 2001

(65) Prior Publication Data

US 2002/0169447 A1 Nov. 14, 2002

(51) Int. Cl.[7] ................................................. A61E 5/04
(52) U.S. Cl. .............................. 606/54; 606/57; 606/59
(58) Field of Search ............................ 606/60, 55, 54, 606/57, 59, 72; 602/22

(56) References Cited

U.S. PATENT DOCUMENTS

| | | | |
|---|---|---|---|
| 4,765,320 A | 8/1988 | Lindemann et al. | |
| 5,232,436 A | 8/1993 | Janevski | |
| 5,376,091 A | 12/1994 | Hotchkiss et al. | |
| 5,387,223 A | 2/1995 | Agee et al. | |
| 5,413,554 A | 5/1995 | Trueman | |
| 5,447,490 A | 9/1995 | Fula et al. | |
| 6,063,087 A | * 5/2000 | Agee et al. | 602/21 |

OTHER PUBLICATIONS

Citron et al., "The use of skeletal traction in the treatment of severe primary Dupuytren's disease," *The Journal of Bone and Joint Surgery*, (1998) 80–B: 126–9.

Messina et al., "The TEC treatment (continuous extension technique) for severe Dupuytren's contracture of the fingers," *Annals of Hand and Upper Limb Surgery* (1991) 10(3): 247–250.

Messina et al., "The continuous elongation treatment by the TEC device for severe Dupuytren's contracture of the fingers," *Plastic and Reconstructive Surgery* (1993) 92: 84.

"When soft tissue is the tissue . . . dynasplint is the solution," Dynasplint Systems, Inc., LaJolla, CA (1996).

"The Joint–Jack Company offers a wide range of therapeutic devices for the ultimate in postoperative handcare," Joint-Jack Company, East Hartford, CT (1994).

"Compass proximal Interphalangeal (PIP) joint hinge, surgical technique," Smith & Nephew (1998).

Product Information Sheet, Padgett Instruments, Inc., Kansas City, MO (prior to May 9, 2001).

Product Information Sheets, Smith & Nephew, Inc., catalogue pp. 42–50, 52–55 (prior to May 9, 2001).

* cited by examiner

*Primary Examiner*—Brian L. Casler
*Assistant Examiner*—Lina R. Kontos
(74) *Attorney, Agent, or Firm*—M. Henry Heines; Townsend and Townsend Crew LLP (57) ABSTRACT

A finger suffering from contracture of the proximal interphalangeal (PIP) joint is treated by application of a device that includes two pivotally joined sections, one of which is securable to the middle phalanx of the finger and the other to another portion of the patient's finger, hand or wrist, with an element that applies torque to the sections. The pivot axis of the two sections is dorsal to the finger, and the torque-producing element and the pivot axis define a moment arm whose length varies in inverse relation to the tension applied to the tensioning element. Torque is applied to the PIP joint without a functionally significant torque being applied to the metacarpal phalangeal (MP) joint, and the device requires attachment only to the dorsal aspect of the phalanx that is distal to the joint being treated rather than to both the distal phalanx and the proximal phalanx.

13 Claims, 8 Drawing Sheets

MEDICAL DEVICE FOR CORRECTING FINGER JOINT CONTRACTURES

BACKGROUND OF THE INVENTION

1. Field of the Invention

This invention addresses injuries and disorders of the musculoskeletal system in general and finger joints in particular, and relates to medical and surgical methods and devices for the correction of these conditions. More particularly this invention provides dynamic orthopedic methods and devices that increase the range of motion of finger joints suffering from contractures.

2. Description of the Prior Art

Skeletal joint contractures (also known as flexion contractures), including fractures and dislocations of joints which reduce the range of motion of the joints, may result from trauma or from burns and the scars left after burns heal. Contractures also result from muscle imbalance across joints and often accompany diseases such as leprosy and Dupuytren's disease. Dupuytren's disease, for example, commonly causes flexion contractures of the small joints of the hand. Any skeletal joint may be subject to disorders or abnormalities of this nature.

Conditions such as these have traditionally been treated by a variety of modalities including splinting, serial plaster casts, and surgical release. Recently, significant innovations have resulted in more effective dynamic methods of treating such injuries in certain joints. One of these innovations is a dynamic finger joint support with a continuous passive motion machine that applies torque to the proximal interphalangeal (PIP) joint to flex and extend the joint. This device is disclosed in U.S. Pat. No. 5,376,091 to Hotchkiss et al., entitled "Dynamic Finger Support," issued Dec. 27, 1994, and incorporated herein by reference. Another innovation is that of Messina et al., as described in Messina, A., et al., "The TEC treatment (continuous extension technique) for severe Dupuytren's contracture of the fingers," *Annals of the Hand and Upper Limb Surgery* 10(3); 247–250 (1991); Messina, A., et al., "The Continuous Elongation Treatment by the TEC Device for Severe Dupuytren's Contracture of the Fingers," *Plastic and Reconstructive Surgery* 92(1): 84–90 (1992); and Citron, N., et al., "The use of skeletal traction in the treatment of severe primary Dupuytren's disease," *The Journal of Bone and Joint surgery* 80-B(1): 126–129 (1998).

A disadvantage of some prior art devices is that the torque that these devices impose to increase the range of motion of the joint is applied through the skin overlying the skeletal segments extending from one or both sides of the joint. An aggravating factor is that the torque must be applied for a significant amount of time before it will successfully increase the range of motion of the joint. If the torque is transmitted to the skeleton indirectly through the skin, the force applied to the skin compromises circulation under the contact site and causes the skin to become tender, red and inflamed. In severe cases, particularly those with compromised sensation, ulcers may develop. For the distal interphalangeal (DIP) joint (the outermost knuckle of the finger) and the proximal interphalangeal (PIP) joint (the middle joint of the finger), the Hotchkiss et al. device avoids this problem by applying force directly to the phalanges that are proximal and distal to the joint being treated, the force being applied through pins embedded in the phalanges themselves through the lateral (side) surfaces of the phalanges. The Messina et al. device similarly applies force through pins embedded laterally in the phalanges distal to the joint being treated and in the hard bones proximal to the joint.

While the Hotchkiss et al. device, the Messina et al. device, and similar devices have achieved success, these devices have certain limitations. Because of the laterally extending pins on these devices and the external elements attached to these pins, these devices are difficult to use on the middle and ring fingers and are instead more useful for joints on the border (index and little) fingers. In addition, the lateral and medial surfaces of the phalanges, particularly those of the proximal phalanges of the fingers, are covered with tendons and other soft tissues that may be punctured when pins are inserted in the sides of these phalanges as Hotchkiss- and Messina-type devices require. A further difficulty is that installation of these devices on the PIP joints of the long or ring fingers necessitates partial spreading of the adjacent fingers, and the spread position must be maintained throughout the treatment period. In general, a Hotchkiss- or Messina-type device on one finger tends to interfere with the use and movement of adjacent fingers and the use of the hand, especially the palmar surface of the hand, for pinching and grasping.

Of potential additional relevance to this invention is U.S. Pat. No. 6,063,087, to Agee et al., entitled "Method and Apparatus for Increasing the Range of Motion of Fingers Suffering From a Limited Range of Motion, Through an External Force Transmitted to the Skeleton," issued May 16, 2000. This patent discloses a device that avoids the use of laterally oriented pins for securement to the proximal and/or middle phalanges, utilizing instead pins that are securable to the dorsal surfaces of the phalanges, especially the dorsal surface of the middle phalanx. Like the Hotchkiss-type devices, the device of U.S. Pat. No. 6,063,087 applies a torque to the PIP joint by way of a torque axis that passes through the joint itself.

Features that would be particularly beneficial in a device for treating contractures of the PIP joint include the following:

(a) the ability to apply a controlled torque to the interphalangeal joint being treated, i.e., a torque that does not deviate widely from a central value as the joint pivots through its full range of motion, (b) the ability to impose a torque on the PIP joint without imposing a significant torque on any other joint including those associated with the same finger, and in general:

(c) a simple construction that combines torque and a wide range of motion to the subject joint throughout the angular range of the joint while maintaining a secure attachment of the device to the patient, (d) ease of manufacture, and (e) adaptability of use for skeletal differences among individual patients.

SUMMARY OF THE INVENTION

The limitations and goals set forth above and others are addressed by the present invention, which resides in a device for treatment of a finger suffering from a disorder involving a limited range of motion of the proximal interphalangeal (PIP) joint of a finger, specifically a contracture of the joint, or for the treatment of such disorders of two or more fingers on the same hand. For the particular finger requiring treatment, the device includes two pivotally joined sections, means for securing the two sections to the patient, and a torque-producing element that produces a torque about the pivot point in a direction that urges the sections toward the parallel. The various components are arranged such that the pivot axis about which the two sections rotate is dorsal to the finger and the torque-producing element and the pivot axis define a moment arm that either remains substantially constant while the torque produced by the torque-producing element varies or decreases as the torque increases. As a result, the device applies a predictable and controllable level of torque to the finger joint throughout the angular range of motion of both the device and the finger joint.

The terms "torque-producing element" and "torque-producing member" are used herein to denote any element that, either by itself or in conjunction with the pivot point, imposes a torque on the PIP joint, The terms therefore encompass elements such as elastic bands or linear springs that are stretched between two points on the device each located at a distance from the pivot point such that by imposing tension between the two sites the band or spring imposes a torque about the pivot point, as well as elements that engage the pivot point itself and create a torque directly.

One of the discoveries arising from this invention is that despite the shift of the pivot axis to a location away from the joint itself, an effective and controllable torque can be applied to the PIP joint as the joint rotates. Another discovery is that when the pivot axis and the torque-producing element are positioned such that the length of the moment arm varies in inverse relation to the force applied to the torque-producing element (i.e., the moment arm lengthens as the torque-producing element is relaxed), the relative positions of the pivot axis and torque-producing element can be adjusted to produce a torque that remains relatively steady as the joint flexes. A further discovery and advantage of the invention are the ability of the device to impose a torque on the PIP joint without imposing a functionally significant torque on any of the neighboring joints, including the metacarpal phalangeal (MP) joint on the same finger. Still further discoveries and advantages will be apparent from the description that follows.

DETAILED DESCRIPTION OF THE INVENTION AND SPECIFIC EMBODIMENTS

While the features and principles that characterize this invention and distinguish it over the prior art may be implemented in a variety of ways and embodied in a variety of constructions, these features and principles can best be understood by examination of specific examples. Several such examples are depicted in the attached figures.

Figure 1:
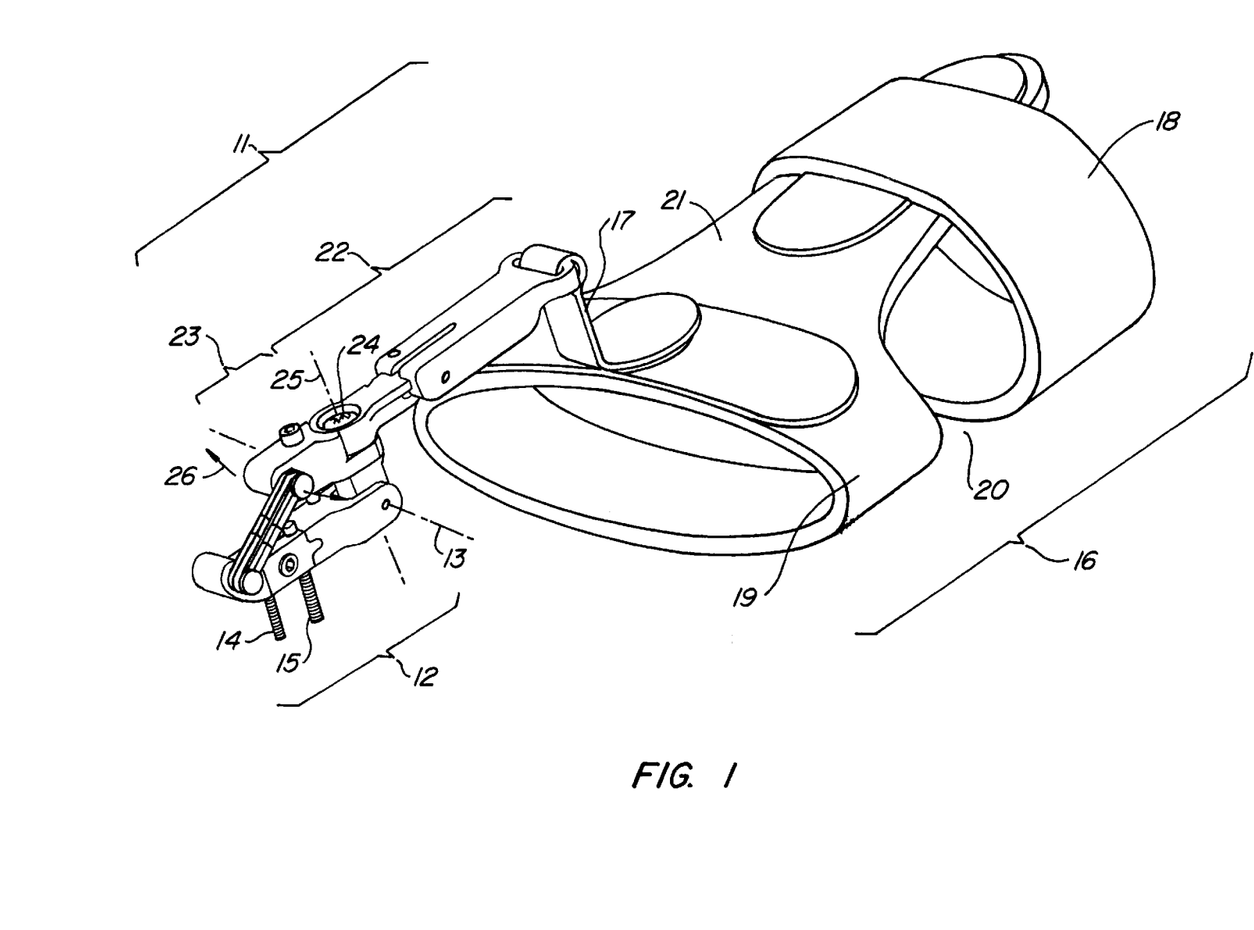
FIG. 1 is a perspective view of one example of a PIP joint contracture treatment device in accordance with this invention.
Figure 2:
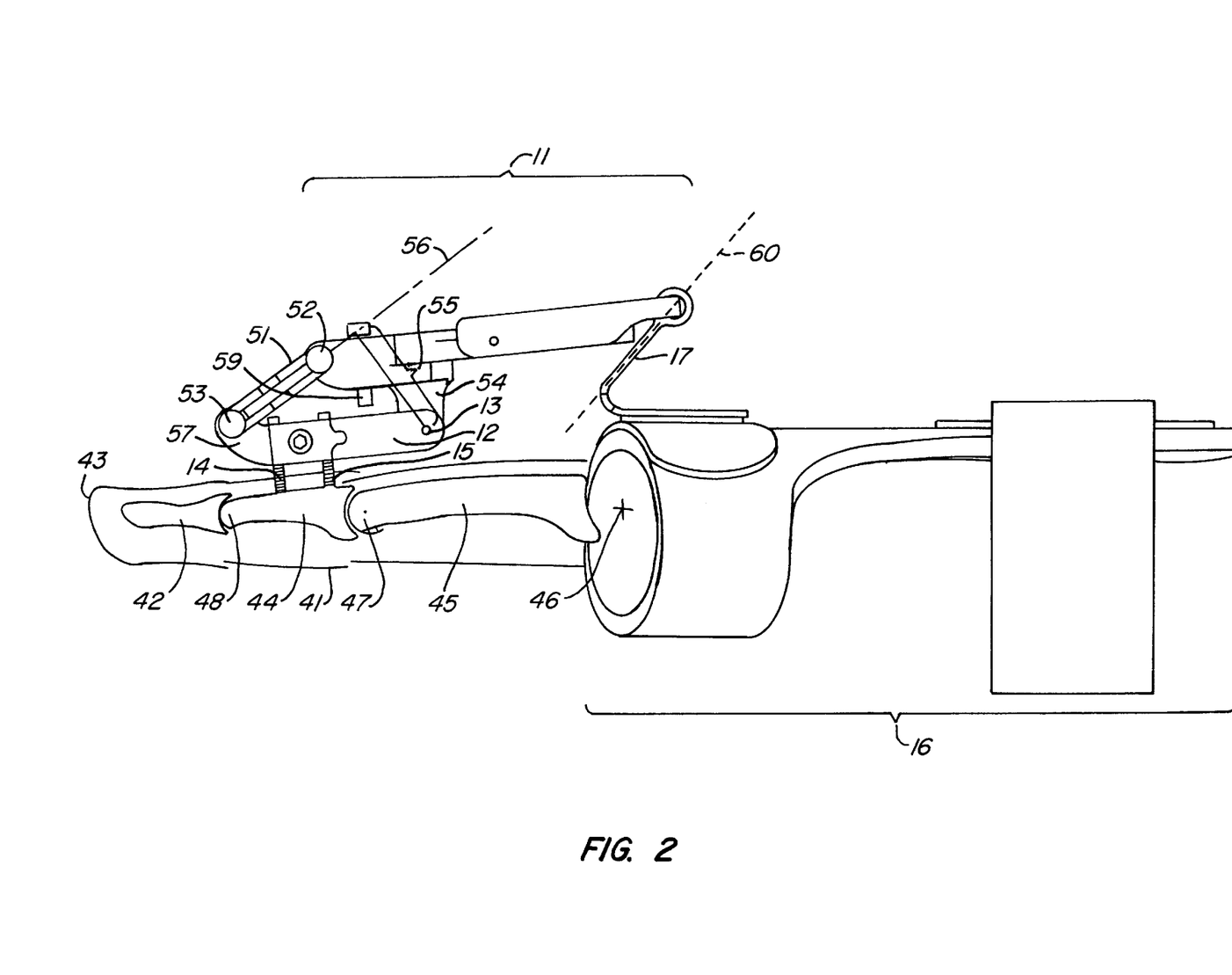
FIG. 2 is a side elevation view of the device of FIG. 1, shown installed on a patient's finger with the finger in its fully extended position.
Figure 3:
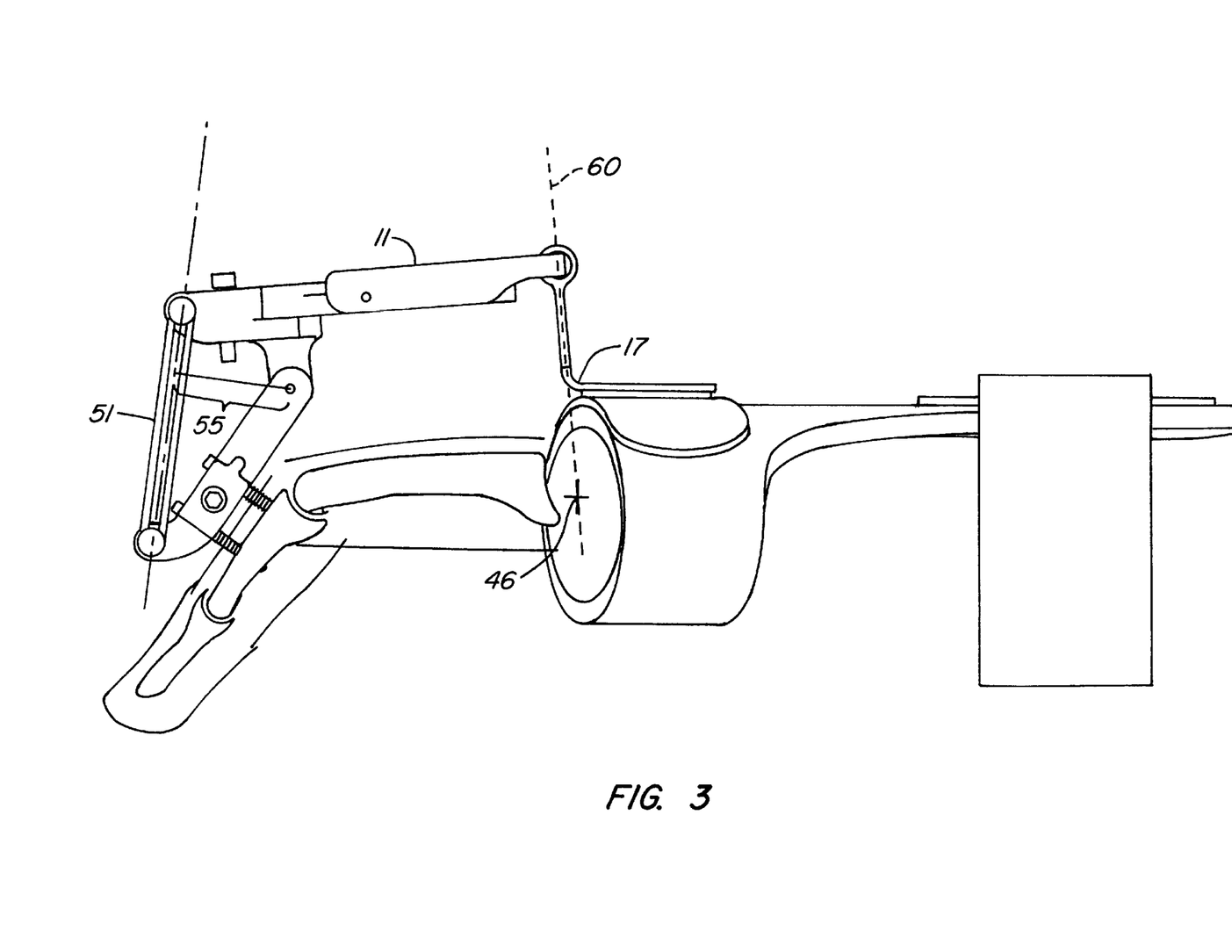
FIG. 3 is a view similar to that of FIG. 2 except that the finger is shown in a partially flexed position.
Figure 4:
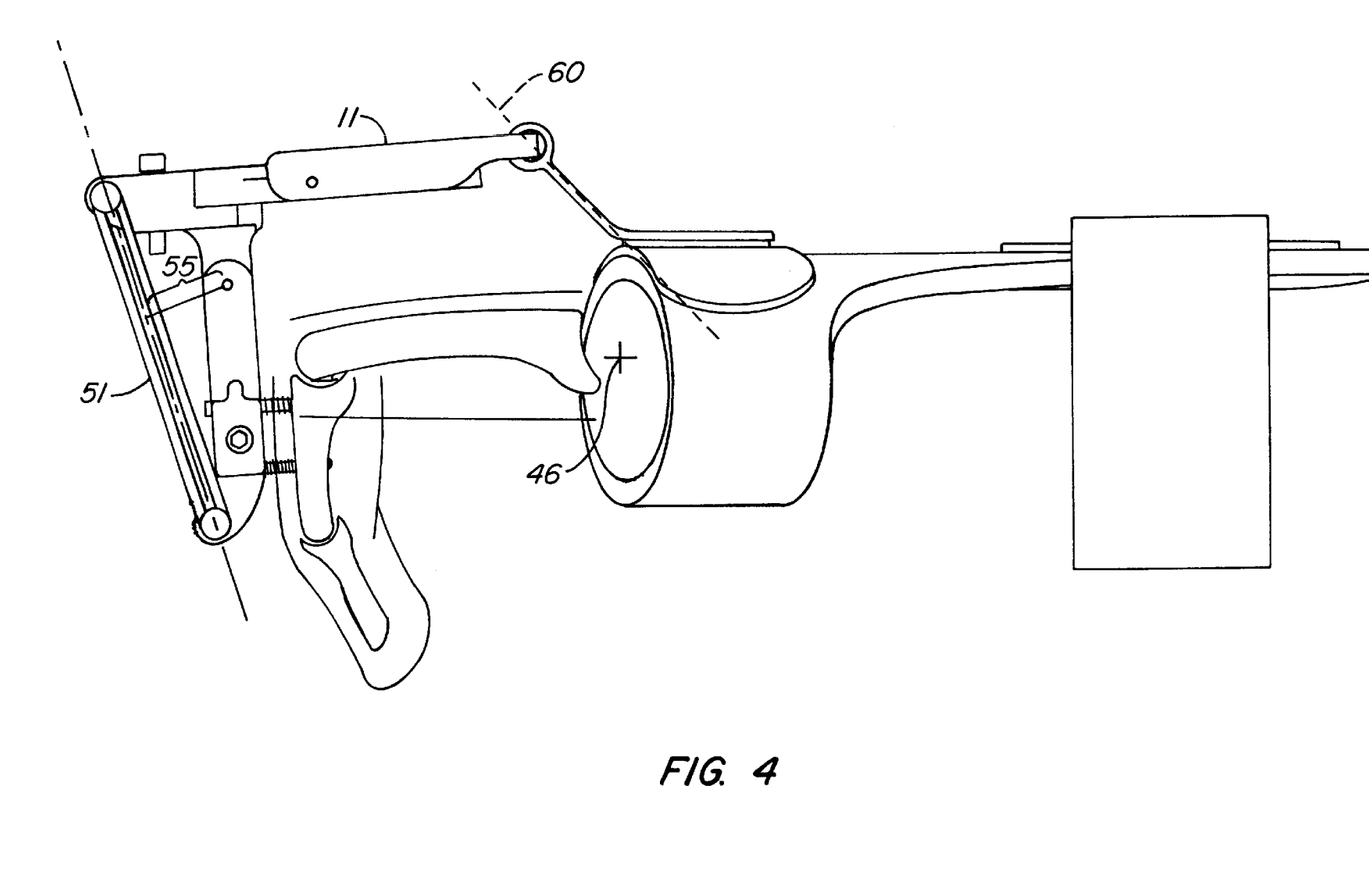
FIG. 4 is a view similar to that of FIG. 2 except that the finger is shown in a fully flexed position.

FIG. 1 is a perspective view from above of a device illustrating an embodiment of the invention that is designed for the correction of a contracture or of a limited range of flexion. The two pivotally joined sections are a proximal support beam 11 and a distal support beam 12, each of which is elongate in shape and primarily straight, and the pivot axis 11 along which these beams are joined is perpendicular to each of the two beams. Attachment of the device to the patient's hand and finger is achieved by a pair of pins 14, 15 extending from the underside of the distal support beam 12 for securement to the middle phalanx through the dorsal surface of the phalanx (as seen in FIG. 2 which is discussed below), in combination with a cuff 16 which encircles the wrist and hand of the patient and is joined to the proximal support beam 11 through a flexible tension-transmitting member 17 or other restraining element.

The term "tension-transmitting member" is used herein to denote a connective element that joins the proximal support beam to the cuff in such a manner that it transmits tension between the proximal support beam and the cuff. The tension-transmitting member may thus be a flexible but nonelastic element such as a strap, string, or chain, or a rigid element such as a rod with end linkages that are rotatable. Other possibilities will be readily apparent to those skilled in the art. In the example shown in FIGS. 1–4, the tension-transmitting member is a strap.

The cuff is constructed in two sections 18, 19 with a gap 20 between the sections, the proximal section 18 intended for encircling the wrist of the patient, and the distal section 19 for encircling the hand of the wearer close to the fingers, with the patient's thumb passing through the gap 20. In the view shown in FIG. 1, the device is oriented such that when worn by a patient, the palm of the patient's hand faces downward. The proximal and distal sections of the cuff 16 in this particular embodiment are individual loops joined by a connecting web 21 with a hook-and-loop-type fastener (VELCRO®). Although the individual loops are depicted as unitary pieces, each individual loop of the cuff can be a strip of fabric or foamed material that can be formed into a loop by a separate hook-and-loop-type fastener. With this construction, the closable strips and the cuff as a whole are easily attachable and removable as well as adjustable to fit hands of different sizes. As with many of the features shown in these drawings, however, these are mere examples, and alternative components or structures that accomplish the same result or a result that is equivalent for the purposes of this invention can be substituted. For example, the cuff material may be woven or unwoven cloth, leather, or any other material, elastic or nonelastic, that would be comfortable to the patient, and the cuff may be constructed in multiple segments as shown or unitary in construction. Alternatively, the cuff may be a molded component to fit the patient's wrist and hand, or the fasteners may be buttons, snaps, buckles, or quick-connect fasteners. Other alternatives will be readily apparent to those skilled in the art.

The flexible strap 17 that joins the proximal support beam 11 to the cuff 16 stabilizes the proximal support beam 11 by limiting the distance by which the beam can be rotated or lifted dorsal to the patient's hand. While any connection that sets a maximum displacement of the beam from the patient's hand can be used, the flexible strap shown in the Figure is an example of preferred embodiments of this invention in which no other constraint is imposed at this location, i.e., no minimum displacement and no tension to the hand when the connection is not stretched to the maximum. Any equivalent connection, such as a loop, ring, or otherwise that restrains the proximal support beam 11 when the finger is flexed can be substituted.

The proximal support beam 11 in this embodiment is constructed in two segments, a proximal segment 22 and a relatively short distal segment 23. These two segments are adjoined by a pivot connection 24, which permits the distal segment 23 of the beam to pivot relative to the proximal segment 22 about a vertical pivot axis 25. The two pivot axes are thus perpendicular, and the direction of pivoting around the second (vertical) axis is indicated by a curved arrow 26. This permits radial-ulnar deviation of the finger.

In the side elevation view of FIG. 2, the device is shown installed on a patient's finger 41, the outline of which is shown over the bone structure. The bone structure consists of the distal phalanx 42 (which terminates in the finger tip 43), the middle phalanx 44, and the proximal phalanx 45. The metacarpal phalangeal (MP) joint 46 join; the proximal phalanx 45 to the hand, the proximal interphalangeal (PIP) joint 47 joins the proximal phalanx 45 to the middle phalanx 44, and the distal interphalangeal (DIP) joint 48 joins the middle phalanx 44 to the distal phalanx 42. The securement pins 14, 15 are threaded pins that penetrate the middle phalanx 44. These pins are surgically drilled through the dorsal cortex of the middle phalanx and extend into the palmar cortex of the phalanx. Preferably, the pins terminate at or above the palmar cortex to avoid injury to the flexor tendons that are located just palmar to the palmar cortex. In this particular embodiment of the invention, two pins are included to provide a rigid connection. Neither the number of pins nor their method of securement to the middle phalanx from the dorsal side are critical to the invention, however, and other means of securement of the distal support beam 12 to the middle phalanx may be used in place of the pins. Examples of such other means are finger cuffs, rings, or bands, or other surgical or nonsurgical techniques.

The torque-producing element that causes the device to apply torque to the PIP joint is represented by an elastic band 51 that is stretched between two mounting posts, one post 52 extending from one side of the distal tip of the proximal support beam 11 and the other post 53 extending from one side of the distal tip of the distal support beam 12. An elastic band is convenient since it is readily removable to facilitate the installation of the device on the patient's hand, and by selecting among different elastic bands or combining two or more elastic bands, one can adjust the torque, add to it or remove it with ease. Elastic bands designed for orthodontic use may be used here. The elastic band is merely an example, however; an equivalent element such as a spring or any other element that exerts a force urging the two mounting posts 52, 53 toward each other or that creates a torque about the pivot axis 13. The tension force applied by the elastic band can be made adjustable by including a row of holes in the proximal support beam to provide alternate positions for the mounting post 52, each stretching the elastic band to successively greater lengths.

In the embodiment of the invention that is shown in FIGS. 1 and 2, the mounting posts 52, 53 and the pivot axis 13 at which the two support beams are joined are arranged such that the tensioning force that draws the mounting posts toward each other causes the distal support beam 12 to become extended parallel to the proximal support beam 11. This extends the PIP joint 47 toward the position shown in FIG. 2. Flexion of the PIP joint 47, as shown to successive degrees in FIGS. 3 and 4, causes extension of the elastic band 51, thereby causing the elastic band to exert an extension torque on the PIP joint.

Returning to FIG. 2, the pivot axis 13 at which the proximal and distal support beams are joined passes through the distal support beam 12 at a location close to the proximal end of that beam. This axis joins the proximal support beam 11 at a location that is toward the end of an extension arm 54 that extends downward from the proximal support beam. The relative positions of the mounting posts 52, 53 and the pivot axis 13 determine the value of a parameter defined herein as the length of the moment arm 55. The moment arm, which is an imaginary line, is the shortest line connecting the pivot axis 13 and the imaginary line 56 that passes through the centers of the two mounting posts 52, 53 to which the elastic band 51 is engaged. The moment arm is thus the perpendicular distance from the straight line 56 defined by the mounting posts to the pivot axis 13.

In the embodiment of the invention shown in FIGS. 1 through 4, the mounting posts 52, 53 and the pivot axis 13 are positioned such that the length of the moment arm 55 decreases as the torque-producing element 51 is elongated, and conversely the length of the moment arm increases as the torque-producing element is shortened. In terms of the flexion of the PIP joint and the torque exerted by the device on the PIP joint, an increase in the flexion is accompanied by an increase in the tension on the elastic band and a decrease in the length of the moment arm, while a decrease in the flexion is accompanied by a decrease in the tension on the elastic band and an increase in the length of the moment arm. This variation is visible by comparison of FIGS. 2, 3, and 4, which show successive increases in the elongation of the elastic band 51 while the length of the moment arm 55 successively decreases. This relationship contributes to the achievement of a torque that remains relatively steady as the PIP joint flexes throughout its the full range. The torque may vary between different degrees of flexion and extension, but remains at a predictable and finite magnitude throughout the full range of joint rotation without sharp increases or decreases. By "finite magnitude" is meant a non-zero value that has a therapeutic effect on the joint condition being treated. A typical average torque may range from 50 to 500 g-cm, and in many cases from 100 to 300 g-cm.

A further feature of the embodiment shown in FIGS. 1 through 4 is a limitation on the degree of extension of the PIP joint. This is achieved by an adjustable stop 59 that extends downward from the proximal support beam 11 and abuts the upper (dorsal) surface of the distal support beam 12. The torque applied to the PIP joint is thus removed when the distal support beam engages the stop. The length by which the stop 59 protrudes toward the distal support beam can be adjustable by using a threaded screw as the stop.

The length of the moment arm and how the length varies with the force exerted by the tensioning element are controlled at least in part by the location of the pivot axis 13 relative to both the PIP joint and the sites 52, 53 on which the torque-producing element is mounted. Further control is achieved in this embodiment by forming the distal support beam 12 so that its distal tip 57 is offset by being turned upward. The position of the pivot axis 13 relative to the PIP joint is determined by the position of the axis relative to the securement pins 14, 15 that secure the distal support beam 12 to the middle phalanx. In this position, the pivot axis 13 is above (distanced from and on the dorsal side of) the proximal phalanx and proximal to the PIP joint (approximately one-quarter to one-half of the distance from the PIP join to the metacarpal phalangeal (MP) joint). The upwardly turned distal tip 57 of the distal support beam lifts the mounting site 53 on that support beam slightly to alter the angle and the range of extension of the torque-producing element 51.

To demonstrate that the device of this invention imposes either no torque or a functionally insignificant torque on the MP joint, attention is again directed to FIGS. 2, 3, and 4, where an imaginary line 60 is drawn along the movable portion of the tension strap 17 that joins the proximal support beam 11 to the cuff 16. Using the flexion-extension axis of the MP joint 46 as a reference point, the line 60 is distal to the MP joint when the PIP joint (and in this example the finger itself) is extended, as shown in the configuration of FIG. 2. In this configuration, the tension strap 17 applies a small torque to the MP joint that tends to flex the MP joint. In the partially flexed position shown in FIG. 3, the line 60 passes through the MP joint and thereby applies no torque at all. With the PIP joint in the fully flexed position shown in FIG. 4, the line 60 has crossed the MP joint and is proximal to the joint. In this configuration, the tension strap 17 applies a small torque to the MP joint that tends to extend the MP joint rather than flex it. Nevertheless, these small torques are functionally insignificant relative to the torques applied to the PIP joint.

Figure 5A:
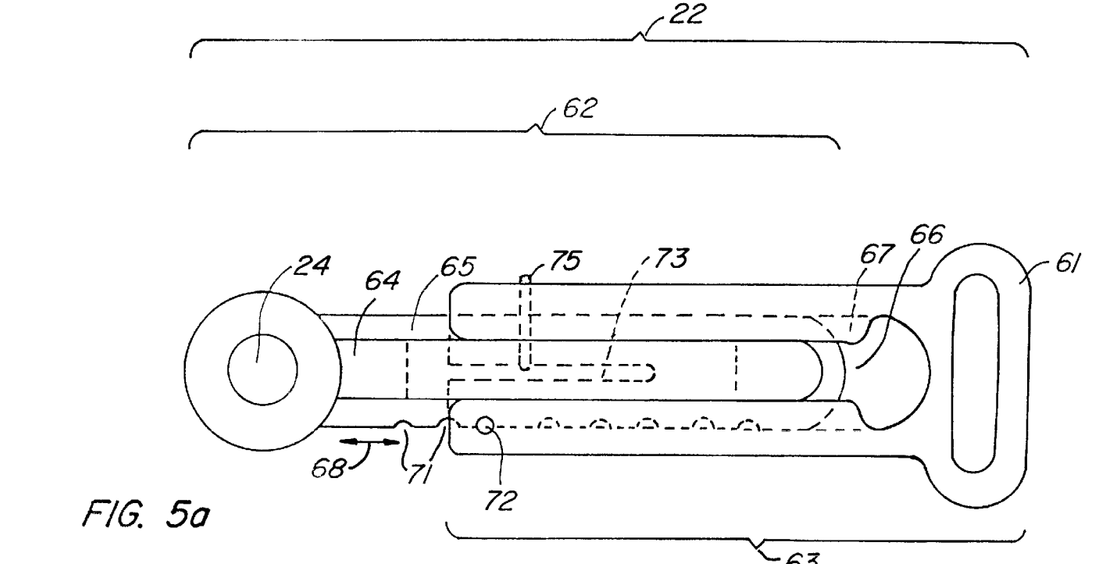
FIG. 5a is a bottom view of a portion of the proximal support beam of the device shown in the preceding figures.
Figure 5B:
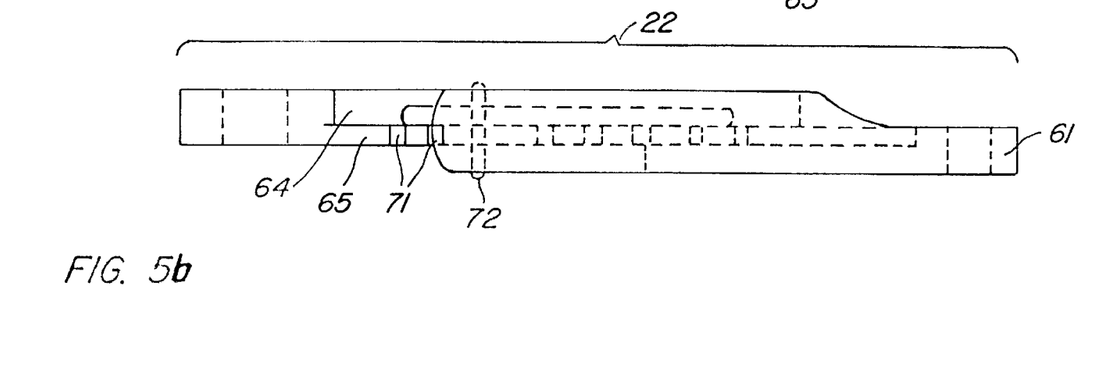
FIG. 5b is a side elevation of the same portion.

The proximal support beam 11 in the embodiment of the invention shown in these figures is constructed in three parts. Two of the parts, identified above as the "proximal segment" 22 and the "distal segment" 23, are labeled as such in FIG. 1. The proximal segment 22 is preferably of adjustable length, and an example of a structure that permits length adjustment is shown in FIGS. 5a and 5b. The proximal end of this structure (i.e., the right end, according to the view shown in FIG. 5) contains a loop 61 through which the flexible strap 17 of FIG. 1 passes, and the distal end (i.e., the left end according to FIG. 5) is circular to accommodate the pivot connection 24 that joins the proximal segment 22 of the support beam to the distal segment 23 (shown in FIG. 1 but not in FIG. 5). The proximal segment itself 22 is constructed in two parts, a notched slide 62 and a sleeve 63.

The notched slide 62 has a central raised area 64 along its longitudinal axis and a flange 65 extending around the periphery of the raised area. The sleeve 63 has an open slot 66 in its bottom surface through which the raised area 64 of the slide protrudes, and a groove 67 (not directly visible: represented by dashed lines) along the interior surface of the slot to receive the flange 65. The flange 65 travels within the groove 67 while the slide is guided by the raised area 64 and slot 66. These elements thus allow the slide to be shifted back and forth within the sleeve as indicated by the arrow 68, as a means of adjusting the combined length of the slide and sleeve and thus the length of the entire proximal section 22. Changes in length are readily made by moving the slide manually within the sleeve.

Fixation of the position of the slide within the sleeve is achieved by a series of notches 71 formed in the flange edge on one side of the slide and a pin 72 passing through the sleeve in a direction transverse to the flange. The pin 72 is sized to he received by each individual notch. The sleeve 63 is sufficiently resilient in construction to flex as the slide is being pushed or pulled between adjacent notches and to snap back to urge the pin 72 into a notch as soon as the notch faces the pin. Contributing to this resiliency is an elongated opening or slot 73 along the top of the sleeve (shown only in dashed lines). The range of motion of the slide 62 and hence the range by which the length of the combined slide and sleeve can be varied are controlled by a lateral slot 74 that extends through the width of the central raised area 64 and a lateral pin 75 that is embedded in the sleeve and extends into the lateral slot 74.

Figure 6:
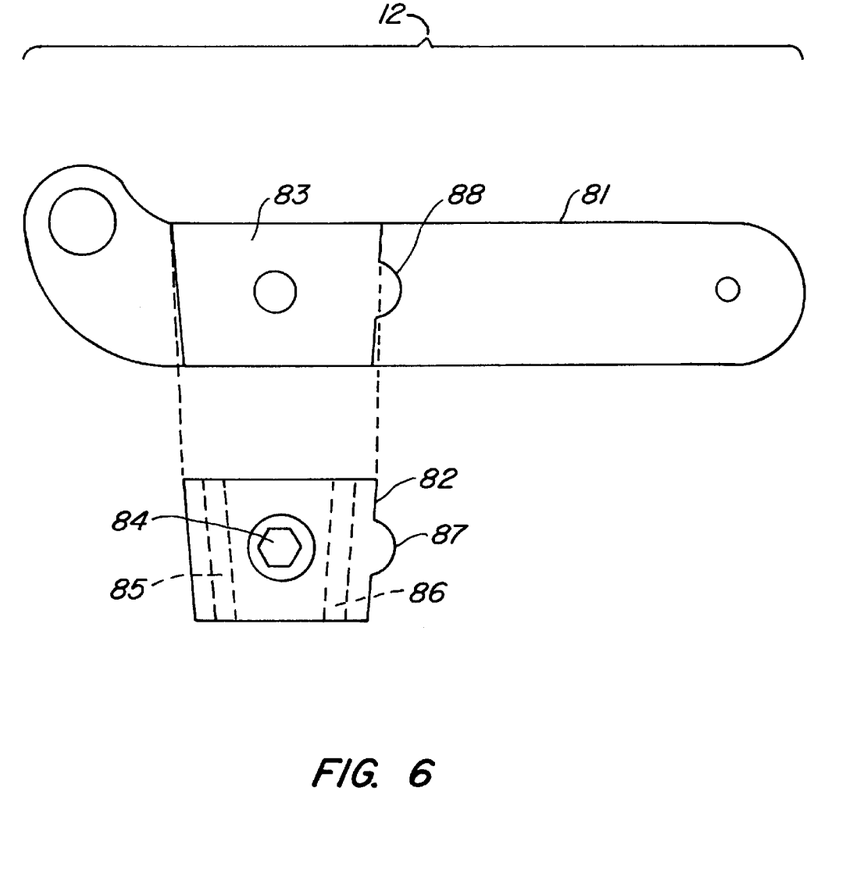
FIG. 6 is a side elevation view of the distal support beam of the device shown in FIGS. 1 through 4, with the clamping plate portion of the beam separated from the remainder of the beam.

As mentioned above, the securement pins 14, 15 are but one example of means for attaching the distal support beam to the middle phalanx. When pins are used, the means by which they can be secured to the distal support beam may vary as well. The enlarged view of the distal support beam shown in FIG. 6 illustrates one method of securing the pins to the beam in a readily detachable manner, permitting the entire device to be removed from the patient's hand and readily replaced at will. The support beam consists of a backing plate 81 and a clamping plate 82 which is sized to fit inside an indentation 83 in the backing plate. A hexagonal fastener 84 (such as one that can be manipulated by an Allen wrench) joins the clamping plate 82 to the backing plate 81. Grooves are formed in the clamping plate 85, 86 (shown in dashed lines) on the side of the clamping plate facing the backing plate 81. The grooves are sized and positioned to receive the securement pins (not shown in the drawing) and to press the pins between the backing plate and clamping plate in a rigid manner. The hexagonal fastener 84 permits the patient or a clinician to connect or disconnect the two plates at will and thereby engage or disengage the device from the patient's finger. The orientation of the pins relative to each other is fixed by the orientation of the grooves 85, 86.

In the particular embodiment shown in FIG. 6, the grooves 85, 86 are not parallel. If the pins are secured to the middle phalanx in a parallel configuration when not under stress, the securement of the exposed ends of the pins between the clamping plate 82 and the backing plate 81 will impart a bending load to the pins, urging the pins into a nonparallel configuration. This will contribute to the fixation of the pins in the distal support beam 12 and add to the rigidity of the attachment of the device to the bone. To assure proper orientation of the clamping plate 82 relative to the backing plate 81 and hence the desired force on the pins exerted by the bending load, the clamping plate contains a knob or protrusion 87 extending from one of its edges to mate with an indentation 88 in the corresponding edge of the backing plate 83.

Figure 7:
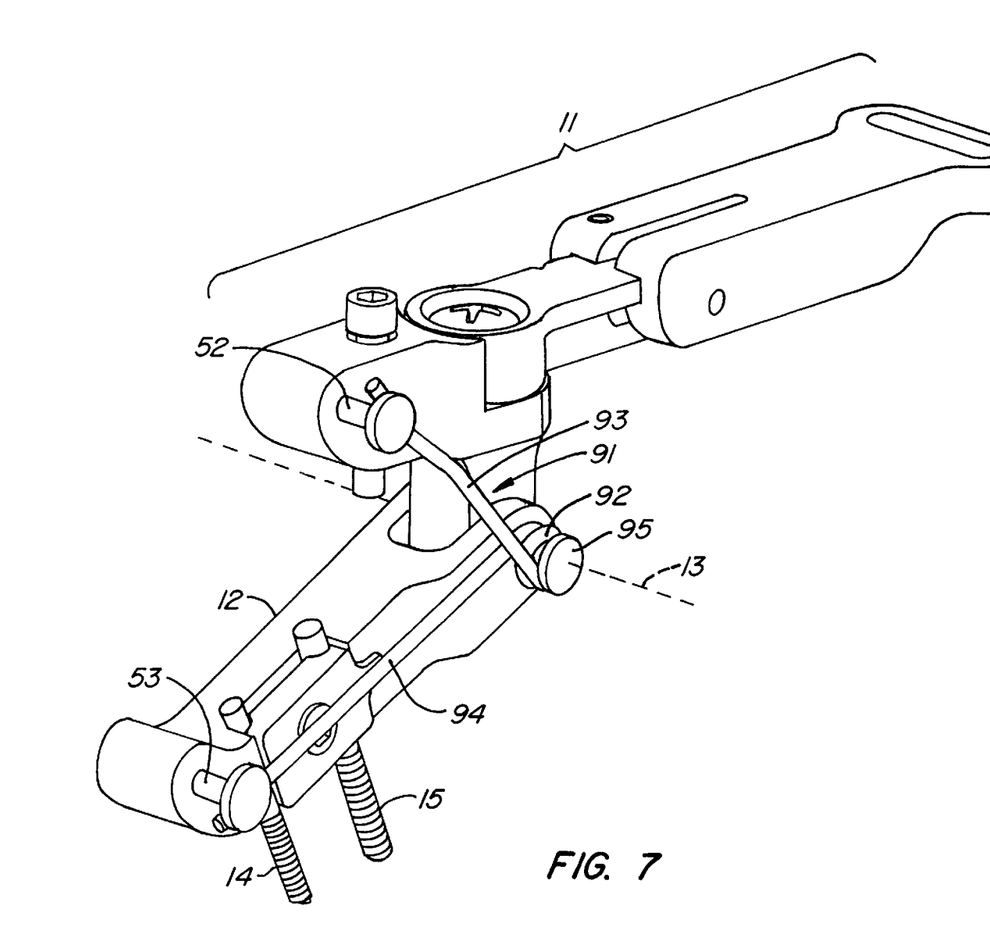
FIG. 7 is a perspective view of a variation on the device shown in FIGS. 1 through 4, the variation residing in the use of a different torque-producing element.

FIG. 7 depicts a device which is a modification of the device shown in the preceding figures. In the device of FIG. 7, a clock spring 91 replaces the elastic band 51 of FIGS. 1 through 4. The clock spring 91 consists of a coiled section 92 with relatively straight arms 93, 94 extending from the two ends of the coiled section. The coiled section 92 encircles a post 95 that extends along the pivot axis 13 where the proximal support beam 11 and the distal support beam 12 are joined, and the two arms 93, 94 extend far enough to contact the outer sides of the two posts 52, 53 which, in the embodiment shown in FIGS. 1 through 4 serve as mounting posts for the elastic band. The coiled section 92 of the spring urges the arms 93, 94 and hence the posts 52, 53 toward each other, thereby urging the support beams and hence the PIP joint toward extension. In this embodiment of the invention, the torque increases with PIP flexion and the moment arm remains constant.

The relation between torque and flexion in the device shown in FIG. 7 can be varied by varying the number of coils in the clock spring and the elastic properties of the wire. With the clock spring shown, which has less than two coils, a given increase in flexion will result in a relatively large increase in torque. Using a clock spring with more coils, such as 6 to 10 for example, the same increase in flexion will still produce an increase in torque but one of significantly less magnitude.

Figure 8:
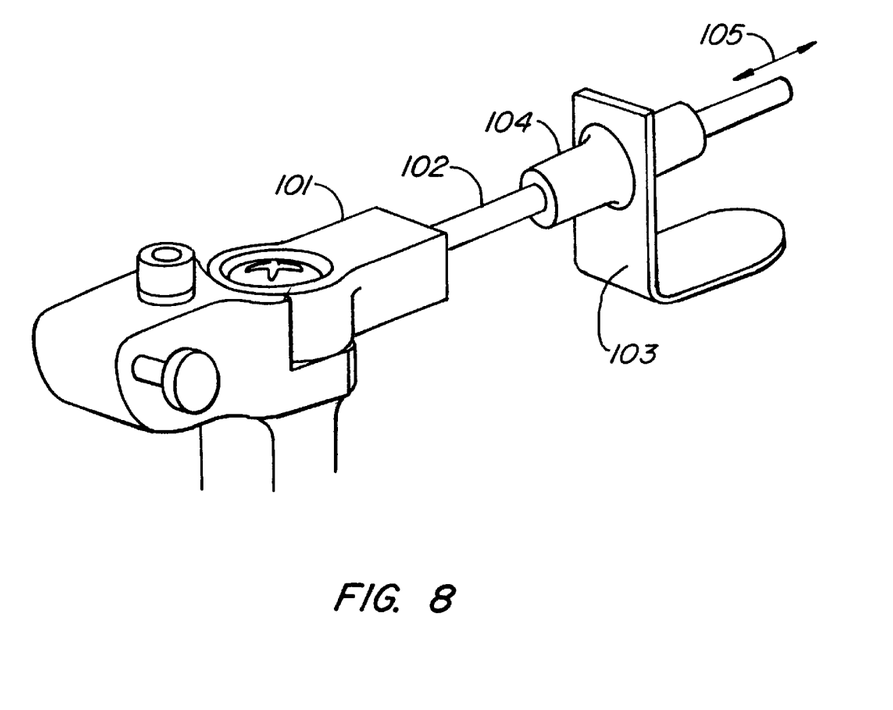
FIG. 8 is a perspective view of a further variation on the device shown in FIGS. 1 through 4, the variation residing in a different construction for securing the proximal support beam to the patient's hand or wrist.

A variation on another element of the device is shown in FIG. 8. This variation is directed to the means by which the proximal support beam 11 (referring to the previous figures) is joined at its proximal end to the cuff 16 through the tension strap 17. The support beam 101 in this variation is constructed with a rod 102 extending from its proximal end, and the tension strap 103 has a linear bearing 104 passing through it. The rod 102 and bearing 104 have a low-friction interface, and the rod is slidably received in the bearing, allowing the rod to slide back and forth in the direction of the arrow 105. This construction allows the rod 102 of the proximal support beam 101 to move back and forth in the linear bearing 104 as the PIP joint is flexed and extended while still restraining the support beam from lifting off of the patient's hand. This allows the tension strap to remain substantially perpendicular to the pushrod, more so than in the construction shown in FIGS. 1–4.

The devices illustrated in the drawings are each designed to treat a single finger on the patient's hand, and can be adjusted to treat any of the fingers other than the thumb by moving the flexible strap 17 to a position that will place the support beams in alignment with the finger to be treated. If the strap is joined to the cuff by a readily movable fastener, such as a hook-and-loop-type fastener, moving the strap is a simple matter. Devices within the scope of this invention can also be constructed to treat two, three or four fingers on the same hand simultaneously, by inclusion of multiples of the support beams and all connecting elements, all for attachment to a common cuff. If a flexible strap 17 and a hook-and-loop-type fastener or equivalent components are used to join the support beams to the cuff, the device is readily modifiable to treat any number of fingers on the hand. When two or more fingers of the same hand are to be treated by a device in accordance with this invention, the device can be designed to apply different torques to the PIP joints of different fingers, by using different torque-producing elements for the different fingers or by modifying the dimensions and shapes of the support beams and the locations of the pivot axes and mounting sites.

The various components of the device described herein may be constructed of any of a variety of materials, preferably lightweight materials that are easily machinable or formable and tend to resist deterioration or breakage due to wear. Examples of suitable materials are steels, aluminum and aluminum alloys, titanium alloys, and semi-rigid polymers such as ultrahigh molecular weight polyethylene and DELRIN® (acetal resins manufactured by E. I. DuPont de Nemours, Wilmington, Del., USA).

The foregoing descriptions are offered for purposes of illustration. Modifications and substitutions of the various elements, their configurations and means of connection and movement, which also fall within the scope of the invention, will be apparent to those skilled in the art upon reading these descriptions.

What is claimed is:

1. A device for attachment to a human finger having proximal, middle, and distal phalanxes, and proximal interphalangeal and metacarpal phalangeal joints, to correct range of motion disorders of said proximal interphalangeal joint by application of a torque biasing said joint toward extension, said apparatus comprising:

proximal and distal support beams joined together in pivotal relation around a pivot axis;

means for rigidly securing said distal support beam to said middle phalanx with said pivot axis dorsal to said finger;

a torque-producing member engaging said proximal support beam and said distal support beam in a manner causing a torque to be applied to said proximal interphalangeal joint, said torque-producing member and said pivot axis defining a moment arm whose change in length relative to increases in said torque is less than or equal to zero; and means for limiting the displacement of said proximal support beam from said proximal phalanx and said metacarpal phalangeal joint, thereby maintaining said torque when said torque-producing member produces torque.

2. A device in accordance with claim 1 in which said torque-producing member and said pivot axis define a moment arm whose length varies inversely relative to increases in said torque.

3. A device in accordance with claim 1 in which said torque-producing member and said pivot axis define a moment arm whose length remains substantially constant upon increases in said torque.

4. A device in accordance with claim 1 in which said means for limiting the displacement of said proximal support beam from said proximal phalanx comprises a cuff for encircling a wrist, a hand, or both, and a tension-transmitting member adjoining said cuff to a proximal end of said proximal support beam.

5. A device in accordance with claim 1 in which said means for limiting the displacement of said proximal support beam from said proximal phalanx and said metacarpal phalangeal joint comprises a cuff for encircling a wrist, a hand, or both, and a linear bearing adjoining said cuff to a proximal end of said proximal support beam.

6. A device in accordance with claim 1 in which said pivot axis is defined as a first pivot axis, and said proximal support beam is comprised of first and second segments joined in pivotal relation around a second pivot axis substantially perpendicular to said first pivot axis to permit lateral movement of said finger.

7. A device in accordance with claim 6 in which said first and second segments of said proximal support beam are proximal and distal relative to each other and thereby defined as proximal and distal segments, and said torque-producing member engages said proximal support beam at a site on said distal segment.

8. A device in accordance with claim 1 in which said proximal support beam comprises means for varying the length thereof.

9. A device in accordance with claim 7 in which said proximal segment comprises means for varying the length thereof.

10. A device in accordance with claim 1 further comprising stop means for imposing a pivoting range limit on said distal support beam relative to said proximal support beam in a direction toward extension of said proximal interphalangeal joint.

11. A device in accordance with claim 1 in which said torque-producing member is removable.

12. A device in accordance with claim 11 in which said torque-producing member is an elastic band.

13. A device in accordance with claim 11 in which said torque-producing member is a clock spring.

* * * * *